United States Patent [19]

Engelson

[11] Patent Number: 4,739,768
[45] Date of Patent: Apr. 26, 1988

[54] CATHETER FOR GUIDE-WIRE TRACKING

[75] Inventor: Erik T. Engelson, Palo Alto, Calif.

[73] Assignee: Target Therapeutics, Los Angeles, Calif.

[21] Appl. No.: 869,597

[22] Filed: Jun. 2, 1986

[51] Int. Cl.⁴ .............................................. A61B 6/00
[52] U.S. Cl. .................................... 128/658; 604/282
[58] Field of Search ..................... 128/656, 658, 768; 604/280, 281, 282

[56] References Cited

U.S. PATENT DOCUMENTS

| | | | |
|---|---|---|---|
| 4,239,042 | 12/1980 | Asai | 604/282 |
| 4,385,635 | 5/1983 | Ruiz | 604/280 |
| 4,417,886 | 11/1983 | Frankhouser et al. | 604/164 |
| 4,545,390 | 10/1985 | Leary | 604/95 |
| 4,655,746 | 4/1987 | Daniels et al. | 604/101 |

*Primary Examiner*—Edward M. Coven
*Assistant Examiner*—Randy Citrin
*Attorney, Agent, or Firm*—Ciotti & Murashige Irell & Manella

[57] ABSTRACT

A catheter for use with a guide wire which can be guided from an external body access site to an internal tissue, and into the tissue along a tortuous path of at least about 5 cm through vessels of less than about 3 mm lumen inner diameter. The catheter includes a relatively stiff proximal segment dimensioned to track the wire from the access site to a region adjacent the internal tissue, and a relatively flexible distal segment dimensioned to track the wire along the tortuous path within the soft tissue.

11 Claims, 1 Drawing Sheet

CATHETER FOR GUIDE-WIRE TRACKING

1. Field of the Invention

The present invention relates to an improved catheter for treating a tissue target site which is accessible by a tortuous path through small vessels.

2. Background of the Invention

Catheters are being used increasingly as a means for delivering diagnostic or therapeutic agents to internal target sites that can be accessed through the circulatory system. For example, in angiography, catheters are designed to deliver a radio-opaque agent to a target site within a blood vessel, to allow radiographic viewing of the vessel and blood flow characteristics near the release site. For the treatment of localized disease, such as solid tumors, catheters allow a therapeutic agent to be delivered to the target site at a relatively high concentration, with minimum overall side effects. Methods for producing localized vaso-occlusion in target tissue regions, by catheter injection of a vaso-occlusive agent, have also been described (co-owned U.S. patent application for "Hyperthermic Treatment of Tumors", Ser. No. 751,605, filed July 2, 1985).

Often the target site which one wishes to access by catheter is buried within a soft tissue, such as brain or liver, and is only reached by a tortuous route through small vessels or ducts—typically less than about 3 mm lumen diameter—in the tissue. The difficulty in accessing such regions is that the catheter must be quite flexible, in order to follow the tortuous path into the tissue, and at the same time, stiff enough to allow the distal end of the catheter to be manipulated from an external access site, which may be as much as a meter or more from the tissue site.

Heretofore, two general methods for accessing such tortuous-path regions have been devised. The first method employs a highly flexible catheter having a inflatable, but pre-punctured balloon at its distal end. In use, the balloon is partially inflated, and carried by blood flow into the target site. The balloon is continually inflated during placement to replenish fluid leaking from the balloon. A major limitation of this method is that the catheter will travel in the path of highest blood flow rate, so many target sites with low blood flow rates cannot be accessed.

In the second prior art method, a torqueable guide wire having a distal bend is guided, by alternately rotating and advancing the wire, to the target site. With the wire in place, the catheter is then advanced along the wire until the distal catheter end is positioned at the target site. An important advantage of this method is the ability to control the location of the catheter along a tortuous path. Torqueable guide wires which can be guided into delicate, tortuous, and narrow vasculature are available. However, it is often difficult or impossible to advance a catheter over the wire, especially where the wire extends along a tortuous path of more than about 10 cm. If the catheter is relatively rigid, it cannot track over the final distal portion of the wire in the tortuous path region, because catheter advancement buckles the wire in a narrow turn, or because catheter advancement pulls the wire out of the distal vessels. On the other hand, catheters having more flexible shafts, such as those used in balloon flow-directed devices, lack the column strength in the catheter's proximal section to be advanced over the guide wire without buckling.

3. Summary of the Invention

It is therefore one general object of the invention to provide a catheter and catheter system which overcome the above-discussed limitations in accessing tortuous path tissue sites by catheter.

A more specific object of the invention is to provide a catheter which can be advanced easily along a guide wire that has been placed in tortuous narrow vasculature.

Still another object of the invention is to provide a method for delivery of an injectable fluid at a tissue site which can be accessed only by a tortuous vascular path.

The invention includes a catheter for use with a guide wire which can be guided from an external body access site to an internal tissue, and into the tissue along a tortuous path of at least about 5 cm through vessels of less than about 3 mm lumen inner diameter. The catheter comprises a relatively stiff proximal segment dimensioned to track the wire from the access site to a region adjacent the internal tissue, and a relatively flexible distal segment dimensioned to track the wire along the tortuous path within the soft tissue.

In a preferred construction, the distal end portion of the proximal segment is formed of inner and outer coaxial tubes, one of which is relatively stiff and one of which is relatively flexible, where the distal segment is a distal extension of the relatively flexible tube. The stiff tube may be formed of polypropylene or high-density polyethylene, and has a preferred wall thickness of about 2–4 mils (thousandths of an inch). The more flexible tube may be formed of low-density polyethylene, or silicon, and also has a preferred wall thickness of about 2–4 mils. The inner diameter of the catheter preferably provides about a 2–5 mil clearance with the guide wire.

In a method for injecting a fluid into a tortuous path site, the guide wire and catheter are moved as a unit to a position adjacent the target tissue. The wire is then advanced ahead of the catheter along the tortuous path within the tissue, followed by catheter tracking over the wire to move the catheter along the path. Fluid is delivered to the target site through the catheter after removal of the guide wire.

These and other objects and features of the invention will become more fully apparent when the following detailed description of the invention is read in conjunction with the accompanying drawings.

DETAILED DESCRIPTION OF THE INVENTION

Figure 1:
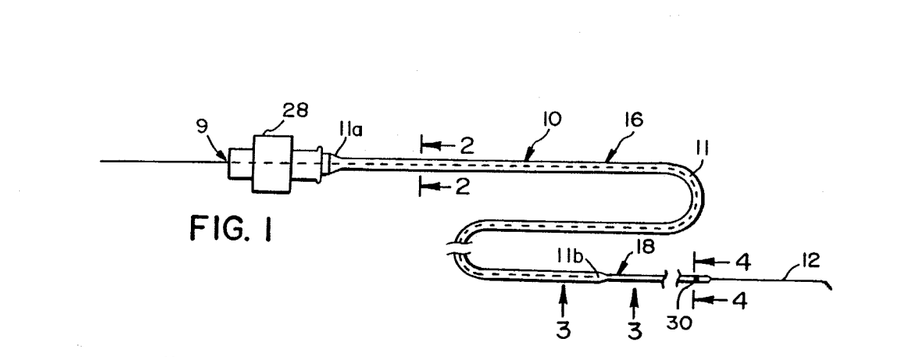
FIG. 1 shows a catheter constructed according to the present invention, and a guide wire used in guiding the catheter to a tortuous-path site within a tissue.

FIG. 1 shows a catheter 10 constructed according to a preferred embodiment of the invention. The catheter is designed for operation in combination with a flexible guide wire, such as wire 12, which is used in guiding the catheter along a tortuous path within a target tissue, in a manner to be described below. The catheter and wire, when used operatively together in a catheter tracking operation to be described below, are referred to collectively as a catheter device. The device is indicated at 9 in FIG. 1.

Figure 2:
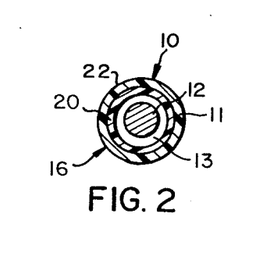
FIG. 2 is an enlarged cross-sectional view taken along section line 2—2 in FIG. 1.

The catheter includes an elongate tubular member 11 having proximal and distal ends 11a, 11b, and an inner lumen 13 (FIGS. 2-4) extending between these ends. According to an important aspect of the invention, the catheter tubular member has a relatively stiff proximal segment 16 which makes up between about 70%-95% of the total length of the tubular member, and a relatively flexible distal segment 18 which makes up the remaining approximately 5%-30% of the length of the tubular member. With reference particularly to FIG. 2, the proximal segment is composed of inner and outer coaxial tubes 20, 22 which are tight-fitting with respect to each other. The stiffness in the proximal segment is provided predominantly by tube 20. The inner, stiffer tube is preferably polypropylene or high-density polyethylene tubing having a final wall thickness (in the assembled catheter) of between about 2-4 mils. The outer, more flexible tube is preferably low-density polyethylene or silicone tubing, also having a preferred wall thickness of between about 2-4 mils. As defined herein, high- and low-density polyethylene have the usual trade meaning which is applied to the density grade of polyethylenes which are commonly used in extrusion.

It will be recognized that other tubing materials whose wall thickness can be adjusted to give comparable tubing flexibilities will be suitable, with the constraint that the combined wall thickness of the two tubes should be less than about 10 mils, and that the number of tubing layers of constant or varying flexibility forming the segments, or portions thereof, can be varied to achieve desired flexibility properties in the tube. It is also recognized that since the outer tube makes a relatively minor contribution to the total stiffness of the proximal segment, the wall thickness of the outer tube will generally be less than about 5 mils.

With reference to FIG. 2, the inner diameter of the proximal segment is dimensioned, with respect to the guide wire, to provide sufficient wire clearance to allow the catheter to be moved easily over the wire in an axial direction, during catheter placement at the target site. The guide wire itself must have a relatively small diameter, to permit its guided movement along a tortuous path in a target tissue. A preferred guide wire designed for accessing a target along a tortuous path has a diameter of between about 8-18 mils. and is formed of a material such as stainless steel which is torqueable, yet flexible in fiber or filament form. Smaller diameter guide wires, such as 8 mil wires, are sufficiently flexible to be manuevered along a tortuous path within a soft tissues. Larger diameter wires, such as 14 and 18 mil wires, may need to be tapered at their distal end regions to manuever along such paths. Guide wires having a tapered-core distal section with a coil wrapping for greater maneuverability in the distal region of the wire are commercially available. The guide wire has or can be fashioned to have a curved tip, for purposes of guiding the wire along a tortuous vascular path.

The inner diameter of the catheter, particularly in its distal segment, is preferably between 2-5 mils larger than the guidewire for which the catheter is designed. Thus, a catheter designed for use with an 18 mil guidewire has a preferred inner diameter of 20-25 mils, and more preferably 21-22 mils. The preferred 2-5 mil total clearance between the wire end inner wall of the segment reduces the tendency of the segment to buckle under compressional strain, since the wire provides column support against tube bending and crimping. Although the inner diameter of the proximal segment may also be 2-5 mils larger than the diameter of the guidewire, and thus provide column support in the distal segment, a larger diameter proximal segment would provide for greater fluid flow through the catheter, in delivering fluid to the target site. In this embodiment, the proximal and distal segments would meet at a step, which would preferably be tapered to provide improved fluid flow.

The optimal length of the proximal segment will vary according to the distance between the tissue region which is to be accessed by the catheter and the externla body site at which the catheter is introduced. For example, where the catheter is introduced at a femoral site, and the target site is in the neck or head region, a relatively long proximal segment of up to 150 cm may be required. Catheters having substantially shorter lengths of about 50-70 cm would, or course, be suitable for applications in which the target tissue can be reached directly from a nearby external access site, such as a brachial artery for a target site in the head and neck.

Figure 3:
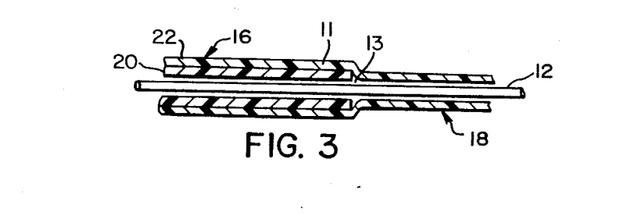
FIG. 3 is an enlarged side sectional view taken along line 3—3 in FIG. 1.
Figure 4:
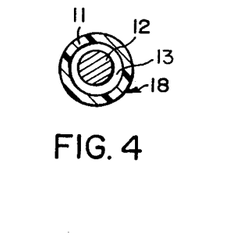
FIG. 4 is an enlarged cross-sectional view taken along line 4—4 in FIG. 1.

With reference now to FIG. 3, it is seen that the proximal segment of the catheter is formed by a distal extension of tube 22 beyond the distal end of tube 20. As indicated above, the proximal segment is formed of relatively flexible tubing, such as low-density polyethylene or silicone, and has a preferred final thickness of between about 2-4 mils. The inner diameter of distal segment is preferably 2-5 mils, and more preferably 3-4 mils larger than the associated guide wire. As noted above, this clearance acts to prevent buckling in the segment, by providing inner columnar support within the segment. At the same time, at least about a 2-5 mil clearance is necessary to accommodate tube distortion which occurs on tracking over a bend in the wire. That is, the 2-5 mil clearance prevents the tube from pinching against the wire in the region of the bend. (The bent tube assumes an oval cross-sectional shape which draws the sides of the tube toward the wire in the plane of the bend.)

A particular catheter embodiment which will be described herein is designed for use with an 18 mil guide wire. The catheter is formed of a polypropylene inner tubing having a final wall thickness (in the finished catheter construction) of about 3 mils, and a low-density polyethylene outer tubing also having a final wall thickness also about 3 mils. The inner diameter of the catheter is between about 21-22 mils along its entire length, and the proximal and distal segments have lengths of about 100 and 10 cm, respectively.

Completing the description of the catheter, the free end of the proximal segment is attached to a fitting 28, such a standard syringe fitting, for use in connecting a syringe to the catheter for fluid injection. At the distal end of the catheter, a radio-opaque band 30, such as a gold or platinum band, serves as a marker for following the position of the catheter radiographically.

The catheter can be formed by extruding an inner tubing of the appropriate material and wall thickness, according to conventional methods. The extruded tubing is then encased by conventional methods, such as heat shrinking, in an outer tubing which has a distal end portion which extends beyond the inner tube. The resulting catheter can be trimmed at one or both ends to produce the desired length proximal and distal segments. The catheter can also be formed by co-extrusion, according to known techniques. Here the two tubing materials are coextruded to form the proximal segment, with only the more flexible tubing material being extruded during the final (or initial) extrusion phase when the distal segment is being formed. In still another method, a relatively stiff tube suitable for the proximal segment of the catheter is placed tightly over a mandrel, and the mandrel and tube then coated, for example, by dipping or spraying with a polymer material, such as silicone which is suitable for forming the flexible distal segment. Alternativelyll, the catheter can be formed by methods in which the flexible distal tube is an extension of the inner, rather than outer, of the coaxial tubes forming the proximal segment.

In addition, it will be recognized that the coaxial arrangement of the catheter tubes, which provides a convenient way to link the relatively stiff tube in the proximal segment to the relatively flexible tube in the distal segment, does not require that the two tubes overlap along the entire proximal segment. That is, the area of overlap needed to join the two segments could be a relatively short portion of the proximal segment. Alternatively, if the materials forming the two catheter segments are heat or solvent fusable, the two segments can be joined end-to-end without tube overlapping.

Following tube construction, the proximal end of the coaxial tube is attached to fitting 28. Band 30 is attached by conventional methods to the end region of the distal segment.

The general two-segment catheter construction can be modified, where desired, for accessing specific types of target areas. For example, to access a target site along a tortuous path which is as much as 25-30 cm in length, the catheter may advantageously include one or more intermediate segments having flexibilities which are intermediate between those of the proximal and distal ends of the catheter. The purpose of the intermediate segment(s) is to provide greater column strength in the distal portion of the catheter which is moved along the tortuous path, but greater flexibility than is provided by the proximal segment of the catheter. In this embodiment, both the distal and intermediate segments are both between about 5-15 cm long, and together comprise between about 10%-40% of the total catheter length. The catheter segments can be formed, by extension of the above constructional principles, of three, two, and one tubing layers, respectively. Since the intermediate segment is used in tracking the wire along its tortuous path, it is considered, for purposes of the present invention, as part of the distal segment. That is, the distal segment can be thought of as including a proximal portion (the intermediate segment) and a distal portion (the most flexible end segment).

In the embodiment above, variable flexibility was built into the portion of the catheter used in following the guide wire along a tortuous path. In another embodiment of a multi-segment catheter, the variable flexibility is in the proximal portion of the catheter used in reaching, but not entering the tortuous-path tissue site. This embodiment may be useful for example, where the distance between the external access site and the target tissue is so great that problems in tube buckling may be encountered in advancing the distal segment toward and into the target tissue. This embodiment too is preferably formed as a multi-layer construction, in which successively more rigid tube segments are built up of successively more layers.

In yet another embodiment, the flexibility along the catheter, or selected portions thereof is made continuously variable, rather than step-wise variable as above. As an example, the distal segment may be continuously more flexible on proceeding toward the free end of the segment. This feature would be advantageous in a relatively long distal segment, especially where the greatest amount of flexibility is required deep within a target tissue.

Figure 5:
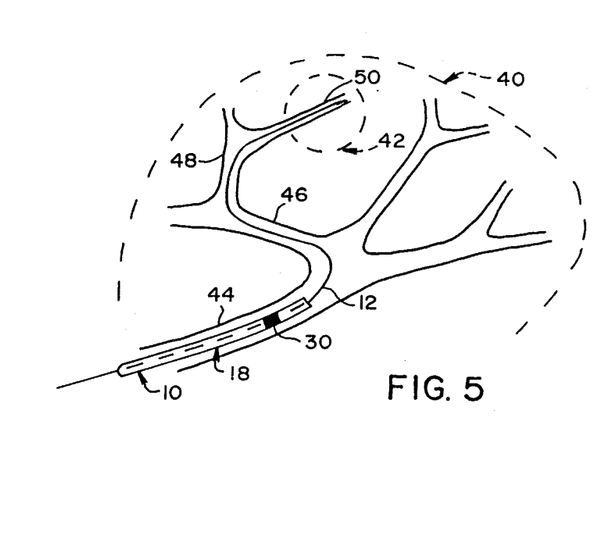
FIG. 5 illustrates a portion of a tortuous path in a soft tissue, and the method of guiding the catheter of the invention along this path.

The method of inserting the catheter into a tissue region which is reached by a tortuous path will be described now with reference to FIG. 5. The figure shows a region of soft tissue 40, such as brain tissue, containing a target site 42 which is to be accessed by the catheter. Initially, the guide wire, such as wire 14, is fed from a vascular access region adjacent the target tissue into a tissue-supply vessel 44 which extends into the tissue. In the present example, the tortuous path to the target site involves vessel 44, a vessel 46 which branches off vessel 44 at more than a right angle, and branch vessel 48, 50, and 52, which each branch off the preceeding vessel as shown. The path shown involves (a) a number of bends, some of which may be 90 degrees or more, (b) small vessels, typically with lumen diameters of less than about 3 mm, and (c) a total path length within the target tissue of at least about 5 cm, typically between about 10-15 cm, and as much as 25 cm.

A path having these characteristics is defined herein as a tortuous path, and is also characterized as being accessible by a guidewire 18 mil or smaller of the type described above, but being too delicate and/or tortuous for accessing by a significantly larger-diameter guidewire.

In operation, the guidewire and catheter are threaded as a unit from an external access site through the vasculature to a region adjacent, but not into the tortuous path region of the target tissue. This is done, in the usual case where the catheter must pass through the cardiac aorta, by first placing a relatively large diameter guiding catheter (e.g., about 40 mils inner diameter) from the access site through the aorta and toward the target site. The present catheter and guidewire are then threaded through the guiding catheter past the aorta, where large-vessel diameters and high blood flow volumes make it difficult or impossible to control the movement and position of the catheter. Once beyond the guiding catheter, the present catheter and guide wire can be independently controlled to move toward the target site. In general, the path from the access site to the region adjacent the tissue is easily accessible, in that sharp bends, small-lumen vessels, and or soft tissue structure are not encountered. The guidewire is then advanced independently along the tortuous path in the target tissue, according to standard wire manipulations, which include rotating or torqueing the wire at each bend, to orient the bend in the wire's distal tip toward next vessel in the path, and then advancing the wire until the next branch is reached.

With the guidewire threaded in place at the target site, the distal catheter is advanced along the wire, encountering first the sharp bend in the guidewire at the juncture of vessels 44, 46. Three features of the catheter are critical for advancing the catheter through this bend without buckling in the distal segment. The first is the flexibility of this segment, which allows the catheter to follow or track the bend without a significant increase in the force required to advance the catheter. That is, the flexible catheter is able to move relatively freely over the bend in the wire in the direction of catheter advance. The second feature is the relatively short length (e.g., 5-15 cm) of the flexible distal segment, and more particularly, the distance along the distal segment from the end of the proximal segment to the bend in the guidewire. The shorter length means greater column strength (strength in resisting axial stress), with reduced tendency to buckle. As described above, with significantly longer path lengths, the distal segment may include one or more distal portions of greater stiffness to provide greater column strength in the catheter along its distal segment. The third feature is the small clearance between the guide wire and inner wall of the distal segment, which acts to provide columnar support for the catheter segment, as indicated above. Also as noted above, the 2-5 mil clearance is sufficient to accommodate the distortion in the distal segment which occurs at bends in the guide wire, without causing appreciable frictional contact between the tube and guidewire, as the tube tracks over the bend. Buckling in the relatively long proximal segment is prevented by the stiffness in the segment combined with the column support provided by the guide wire.

With the catheter moved to the target site, the guide wire is withdrawn to allow a fluid material to be injected into the site. The injected material may include: (1) radio-opaque agents for viewing blood vessel anatomy and blood flow characteristics in the target region, (2) vaso-occlusive agents, such as a suspension of collagen fibers, which can be used to produce small-artery vaso-occlusions in the tissue region region supplied by the target vessel; and (3) pharmacological agents, such as anti-tumor drugs, which are effective against identified disease states at the target site.

From the foregoing, it can be appreciated how various objects and features of the invention are met. The novel catheter construction described herein allows for tracking along a tortuous path over a guide wire without buckling by virtue of (1) the relatively flexible distal portion which tracks over the wire along the tortuous path, (2) the relatively stiff proximal portion which extends over a major portion of the catheter length, and (3) the guidewire clearance within the catheter which provides column support, particularly within the distal segment, while still accommodating distortion in the segment in the region of bending. The catheter is easily constructed and is operable with known types of guidewires.

The catheter is useful in delivering diagnostic, therapeutic, or vaso-occlusive agents to deep tissue sites which have heretofore been relatively inaccessible to catheters.

While preferred embodiments of the invention have been described herein, it will be recognized that a variety of changes and modifications can be made without departing from the invention.

It is claimed:

1. A catheter for use with a guide wire which can be guided from an external body access site to an internal tissue, and into the tissue along a tortuous path of at least about 5 cm through vessels of less than about 3 mm lumen inner diameter, said catheter comprising an elongate tubular member having proximal and distal ends, and an inner lumen extending between these ends, said member being composed of a relatively stiff proximal segment means for tracking the wire from the access site to a region adjacent the internal tissue, and a relatively flexible distal segment means at least about 5 cm long for tracking the wire along the tortuous path within the internal tissue.

2. The catheter of claim 1, slidably receiving a guide wire having a specified diameter, wherein the distal segment has an inner diameter which is between about 2-5 mils larger than the specified diameter of the guide wire.

3. The catheter of claim 2, wherein the lumen of the tubular member has a substantially uniform inner diameter along said distal segment.

4. The catheter of claim 1, wherein at least a distal end portion of the proximal segment of the tubular member is formed of inner and outer coaxial tubes, one of which is relatively stiff and one of which is relatively flexible, and the distal segment is a distal extension of the relatively flexible tube.

5. The catheter of claim 4, wherein the relatively stiff tube is formed of a polymeric material selected from the group consisting of polypropylene and high-density polyethylene, and the relatively flexible tube is formed of low-density polyethylene.

6. The catheter of claim 5, wherein the tubes each have a wall thickness of between about 2 and 4 mils.

7. The catheter of 4, wherein the outer tube extends substantially the entire length of the catheter.

8. The catheter of claim 1, for use in accessing a site within the brain, wherein the proximal segment has a total length of between about 60-150 cm, and the distal segment has a total length of between about 10-15 cm.

9. A catheter device for use in accessing a target site located within a tissue along a tortuous path of at least about 5 cm through vessels of less than about 3 mm lumen inner diameter, said device comprising a guide wire which can be guided from an external body access site to the tissue, and into the tissue along the tortuous path to the target site, and an elongate tubular member having proximal and distal ends, and an inner lumen extending between these ends, and through which the wire is slidably carried, said member being composed of a relatively stiff proximal segment means for tracking the wire from the access site to a region adjacent the internal tissue, and a relatively flexible distal segment means at least about 5 cm long, for tracking the wire along the tortuous path within the internal tissue.

10. The device of claim 9, wherein the guide wire has a specified diameter and the distal segment of the tubular member has an inner diameter which is between about 2-5 mils larger than said specified diameter.

11. The device of claim 9, wherein a distal end portion of the proximal segment of the tubular member is formed of inner and outer coaxial tubes, one of which is relatively stiff, and one of which is relatively flexible, the distal segment is a distal extension of the relatively flexible tube, the relatively stiff tube is formed of a polymeric material selected from the group consisting of polypropylene and high-density polyethylene, and the relatively flexible tube is formed of low-density polyethylene.

* * * * *

REEXAMINATION CERTIFICATE (2430th)
United States Patent [19]
Engelson

[11] B1 4,739,768

[45] Certificate Issued Nov. 15, 1994

[54] CATHETER FOR GUIDE-WIRE TRACKING

[75] Inventor: Erik T. Engelson, Palo Alto, Calif.

[73] Assignee: Target Therapeutics, Fremont, Calif.

Reexamination Request:
No. 90/003,095, Jun. 16, 1993

Reexamination Certificate for:
Patent No.: 4,739,768
Issued: Apr. 26, 1988
Appl. No.: 869,597
Filed: Jun. 2, 1986

[51] Int. Cl.⁵ .............................................. A61B 6/00
[52] U.S. Cl. .................................. 128/658; 604/282

[56] References Cited

U.S. PATENT DOCUMENTS

| | | | |
|---|---|---|---|
| 4,464,176 | 8/1984 | Wijayarathna | 604/164 |
| 4,592,341 | 6/1986 | Omagari et al. | 128/4 |
| 4,690,175 | 9/1987 | Ouchi et al. | 604/282 |
| 4,842,590 | 6/1989 | Tanabe et al. | 128/656 |

FOREIGN PATENT DOCUMENTS

0102685  3/1984  European Pat. Off. .

*Primary Examiner*—Randy Shay

[57] ABSTRACT

A catheter for use with a guide wire which can be guided from an external body access site to an internal tissue, and into the tissue along a tortuous path of at least about 5 cm through vessels of less than about 3 mm lumen inner diameter. The catheter includes a relatively stiff proximal segment dimensioned to track the wire from the access site to a region adjacent the internal tissue, and a relatively flexible distal segment dimensioned to track the wire along the tortuous path within the soft tissue.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-11 are cancelled.

New claims 12-49 are added and determined to be patentable.

*12. A catheter for use with a guide wire, which catheter can be guided from an external body access site to an internal tissue, and into the tissue along a tortuous path of at least about 5 cm through vessels of less than about 3 mm lumen inner diameter to a target site, said catheter comprising:*

*an elongate tubular member being sufficiently flexible that to travel along a tortuous path of at least 5 cm. through vessels of less than about 3 mm. to said target site said elongate tubular member must be guided with a guide wire, said elongate tubular member having proximal and distal ends, an outer surface and an inner surface defining an inner lumen extending between those ends, said elongate tubular member being composed of*

*a relatively stiff proximal segment for tracking the guide wire from the access site to a region adjacent the internal tissue, and*

*a relatively flexible distal segment at least about 5 cm long for tracking the guide wire from said region along said tortuous path of at least about 5 cm. through vessels of about 3 mm. within the internal tissue to the target site, said flexible distal segment having both a proximal portion and a distal portion, which distal portion is more flexible than the proximal portion and is of outer diameter, wall thickness, and composition to cause the distal portion of the distal segment to be sufficiently flexible to track the guide wire to the target site along the tortuous path provided by the guide wire in the internal tissue and where the proximal portion of the distal segment comprises one or more intermediate portions having flexibilities between those of the proximal segment and the distal portion of the distal segment.*

*13. The catheter of claim 12, where the proximal portion comprises one intermediate portion.*

*14. The catheter of claim 12, slidably receiving a guide wire having a specified diameter, where the distal segment has an inner diameter which is between about 2-5 mils larger than the specified diameter of the guide wire.*

*15. The catheter of claim 14, where the lumen of the tubular member has a substantially uniform inner diameter along said distal segments.*

*16. The catheter of claim 12, where at least a distal end portion of the proximal segment of the tubular member is formed of inner and outer coaxial tubes, one of which is relatively stiff and one of which is relatively flexible, and the distal segment is a distal extension of the relatively flexible tube.*

*17. The catheter of claim 16, where the relatively stiff tube is formed of a polymeric material selected from the group consisting of polypropylene and high-density polyethylene, and the relatively flexible tube is formed of low-density polyethylene.*

*18. The catheter of claim 17, where the tubes each have a wall thickness of between about 2 and 4 mils.*

*19. The catheter of claim 16, where the outer tube extends substantially the entire length of the catheter.*

*20. The catheter of claim 12, for use in accessing a site within the brain, where the proximal segment has a total length of between about 60-150 cm., and the distal segment has a total length of between 10-15 cm.*

*21. The catheter of claim 12 where said distal portion of the distal segment of the tubular member comprises a single layer polymeric tube defining the inner lumen in the distal portion and defining the outer surface.*

*22. The catheter of claim 12 wherein said distal portion of the distal segment of the tubular member comprises a polymeric layer defining the inner surface in the distal portion.*

*23. The catheter of claim 22 wherein said distal portion of the distal segment of the tubular member further comprises a polymeric outer surface on said distal portion.*

*24. The catheter of claim 12 wherein said distal portion of the distal semgnet of the tubular member comprises a polymeric tubing, the sole polymeric component of which is in the form of a single layer of polymer.*

*25. The catheter of claim 12 in which the distal portion can traverse a 90 bend in a 3 mm. vessel.*

*26. A catheter device for use in accessing a target site located within a tissue along a tortuous path of at least about 5 cm through vessels of less than about 3 mm lumen inner diameter to a target site, said catheter device comprising*

*a guide wire which can be guided from an external body access site to the tissue, and into the tissue along the tortuous path to the target site, and*

*an elongate tubular member that is received over said guide wire and tracked therealong to the target site, said elongate tubular member being sufficiently flexible that to travel along a tortuous path of at least 5 cm. through vessels of less than about 3 mm. to said target site said elongate tubular member must be guided with a guide wire, and said elongate tubular member having porixmal and distal ends, an outer surface and an inner surface defining an inner lumen extending between those ends, and through which the guide wire is slidably carried, said elongate tubular member being composed of*

*a relatively stiff proximal segment for tracking the guide wire from the access site to a region adjacent the internal tissue, and*

*a relatively flexible distal segment at least about 5 cm long for tracking the guide wire from said region along said tortuous path of at least about 5 cm. through vessels of about 3 mm. within the internal tissue to the target site, said flexible distal segment having both a proximal portion and a distal portion, which distal portion is more flexible than the proximal portion and is of outer diameter, wall thickness, and composition to cause the distal portion of the distal segment to be sufficiently flexible to track the guide wire to the target site along the tortuous path provided by the guide wire in the internal* tissue and where the proximal portion of the distal segment comprises one or more intermediate portions having flexibilities between those of the proximal segment and the distal portion of the distal segment.

27. The device of claim 26, where the proximal portion comprises one intermediate portion.

28. The device of claim 26, where the guide wire has a specified diameter, and the distal segment of the tubular member has an inner diameter which is between about 2–5 mils larger than said specified diameter.

29. The catheter of claim 28 for use in accessing a site within the brain, where the proximal segment has a total length of between about 60–150 cm, and the distal segment has a total length of between about 10–15 cm.

30. The device of claim 26, where a distal end portion of the proximal segment of the tubular member is formed of inner and outer coaxial tubes, one of which is relatively stiff, and one of which is relatively flexible, the distal segment is a distal extension of the relatively flexible tube, the relatively stiff tube is formed of a polymeric material selected from the group consisting of polypropylene and high-density polyethylene, and the relatively flexible tube is formed of low-density polyethylene.

31. A catheter for use with a guide wire which can be guided from an external body access site to an internal tissue, and into the tissue along a tortuous path of at least about 5 cm through vessels of less than about 3 mm lumen inner diameter to a target site, said catheter comprising:
an elongate tubular member that is adapted to be received over said guide wire and tracked therealong to the target site, said elongate tubular member being sufficiently flexible that to travel along a tortuous path of at least 4 cm. through vessels of less than about 3 mm. to said target site said elongate tubular member must be guided with a guide wire, and said elongate tubular member having proximal and distal ends, an outer surface and an inner surface defining an inner lumen extending between those ends, said elongate tubular member being composed of
a relatively stiff proximal segment for tracking the guide wire from the access site to a region adjacent the internal tissue, and
a relatively flexible distal segment at least about 5 cm long for tracking the guide wire from said region along said tortuous path of at least about 5 cm. through vessels of about 3 mm. within the internal tissue to the target site, where at least one segment has increasing flexibility distally and at least the most distal 5 cm. of said distal segment is of outer diameter, wall thickness, and composition to cause the distal portion of the distal segment to be sufficiently flexible to track the guide wire to the target site along the tortuous path provided by the guide wire in the internal tissue.

32. The catheter of claim 31, where the distal segment is continuously more flexible towards the distal end of the distal segment.

33. The catheter of claim 31 where the proximal segment has variable flexibility.

34. The catheter of claim 31, slidably receiving a guide wire having a specified diameter, where the distal segment has an inner diameter which is between about 2–5 mils larger than the specified diameter of the guide wire.

35. The catheter of claim 34, where the lumen of the tubular member has a substantially uniform inner diameter along said distal segments.

36. The catheter of claim 31, where at least a distal end portion of the proximal segment of the tubular member is formed of inner and outer coaxial tubes, one of which is relatively stiff and one of which is relatively flexible, and the distal segment is a distal extension of the relatively flexible tube.

37. The catheter of claim 36, where the outer tube extends substantially the entire length of the catheter.

38. The catheter of claim 36, where the relatively stiff tube is formed of a polymeric material selected from the group consisting of polypropylene and high-density polyethylene, and the relatively flexible tube is formed of low-density polyethylene.

39. The catheter of claim 38, where the tubes each have a wall thickness of between about 2 and 4 mils.

40. The catheter of claim 31 in which the distal portion can traverse a 90 bend in a 3 mm. vessel.

41. A catheter device for use in accessing a target site located within a tissue along a tortuous path of at least about 5 cm through vessels of less than about 3 mm lumen inner diameter to a target site, said catheter device comprising
a guide wire which can be guided from an external body access site to the tissue, and into the tissue along the tortuous path to the target site, and
an elongate tubular member that is received over said guide wire and tracked therealong to the target site, said elongate tubular member being sufficiently flexible that to travel along a tortuous path of at least 5 cm. through vessels of less than about 3 mm. to said target site said elongate tubular member must be guided with a guide wire, and said elongate tubular member having proximal and distal ends, an outer surface and an inner surface defining an inner lumen extending between these ends, and through which the guide wire is slidably carried, said elongate tubular member being composed of
a relatively stiff proximal segment for tracking the guide wire from the access site to a region adjacent the internal tissue, and
a relatively flexible distal segment at least about 5 cm long for tracking the guide wire from said region along said tortuous path of at least about 5 cm. through vessels of about 3 mm. within the internal tissue to the target site, where at least one segment has increasing flexibility distally and at least the most distal 5 cm. of said distal segment is of outer diameter, wall thickness, and composition to cause the distal portion of the distal segment to be sufficiently flexible to track the guide wire to the target site along the tortuous path provided by the guide wire in the internal tissue.

42. The catheter of claim 41, where the distal segment is continuously more flexible towards the distal end of the distal segment.

43. The catheter of claim 41 where the proximal segment has increasing flexibility distally.

44. The device of claim 41, where the guide wire has a specified diameter, and the distal segment of the tubular member has an inner diameter which is between about 2–5 mils larger than said specified diameter.

45. The device of claim 41, where at least a distal end portion of the proximal segment of the tubular member is formed of inner and outer coaxial tubes, one of which is relatively stiff, and one of which is relatively flexible, the distal segment is a distal extension of the relatively flexible tube, the relatively stiff tube is formed of a polymeric material selected from the group consisting of polypropylene and high-density polyethylene, and the relatively flexible tube is formed of low-density polyethylene.

46. A catheter for use with a guide wire, which catheter can be guided from an external body access site to an internal tissue, and into the tissue along a tortuous path of at least about 5 cm through vessels of less than about 3 mm lumen inner diameter to a target site, said catheter comprising:

an elongate tubular member being sufficiently flexible that to travel along a tortuous path of at least 5 cm. through vessels of less than about 3 mm. to said target site said elongate tubular member must be guided with a guide wire, said elongate tubular member having proximal and distal ends, an outer surface and an inner surface defining an inner lumen extending between these ends, said elongate tubular member being composed of a relatively stiff proximal segment for tracking the guide wire from the access site to a region adjacent the internal tissue, and a relatively flexible distal segment at least about 5 cm long for tracking the guide wire from said region along said tortuous path of at least about 5 cm. through vessels of about 3 mm. within the internal tissue to the target site, said flexible distal segment having both a proximal portion and a distal portion, which distal portion is more flexible than the proximal portion and is of outer diameter, wall thickness, and composition to cause the distal portion of the distal segment to be sufficiently flexible to track the guide wire to the target site along the tortuous path provided by the main guide wire in the internal tissue and where the proximal portion of the distal segment comprises one or more intermediate portions having flexibilities between those of the proximal segment and the distal portion of the distal segment and where said distal portion of the distal segment of the tubular member consists essentially of a single layer of a polymeric material.

47. The catheter of claim 46, where the proximal portion comprises one intermediate portion.

48. The catheter of claim 46 also comprising a guide wire which can be guided from an external body access site to the internal tissue, and into the internal tissue along the tortuous path to the target site and over which guide wire the elongate tubular body may be slidably passed to the target site.

49. The catheter of claim 46 in which the distal portion can traverse a 90 bend in a 3 mm. vessel.

* * * * *

REEXAMINATION CERTIFICATE (2701th)
United States Patent [19]
Engelson

[11] B2 4,739,768
[45] Certificate Issued Oct. 24, 1995

[54] CATHETER FOR GUIDE-WIRE TRACKING

[75] Inventor: Erik T. Engelson, Palo Alto, Calif.

[73] Assignee: Target Therapeutics, Fremont, Calif.

Reexamination Requests:
No. 90/003,582, Aug. 22, 1994
No. 90/003,787, Mar. 15, 1995
No. 90/003,856, Apr. 7, 1995

Reexamination Certificate for:
Patent No.: 4,739,768
Issued: Apr. 26, 1988
Appl. No.: 869,597
Filed: Jun. 2, 1986

Reexamination Certificate B1 4,739,768 issued Nov. 15, 1994.

[51] Int. Cl.$^6$ .................................... A61B 6/00
[52] U.S. Cl. ............................ 128/658; 604/282
[58] Field of Search ................. 128/656, 658, 128/768; 604/280, 281, 282

[56] References Cited

U.S. PATENT DOCUMENTS

| | | |
|---|---|---|
| 2,437,542 | 3/1948 | Krippendorf . |
| 3,406,685 | 10/1968 | May . |
| 3,416,531 | 12/1968 | Edwards . |
| 3,605,750 | 9/1971 | Sheridan et al. . |
| 3,618,613 | 11/1971 | Schulte . |
| 3,618,614 | 11/1971 | Flynn . |
| 3,789,841 | 2/1974 | Antoshkiw . |
| 3,935,857 | 2/1976 | Co . |
| 3,965,909 | 6/1976 | Waddell et al. . |
| 4,020,829 | 5/1977 | Willson et al. . |
| 4,044,765 | 8/1977 | Kline . |
| 4,117,836 | 10/1978 | Erikson . |
| 4,239,042 | 12/1980 | Asai . |
| 4,279,252 | 7/1981 | Martin . |
| 4,280,500 | 7/1981 | Ono . |
| 4,318,402 | 3/1982 | Vaillancourt . |
| 4,385,635 | 5/1983 | Ruiz . |
| 4,417,886 | 11/1983 | Frankhouset et al. . |
| 4,425,919 | 1/1984 | Alston, Jr. et al. . |
| 4,430,083 | 2/1984 | Ganz et al. . |
| 4,437,857 | 3/1984 | Goldstein et al. . |
| 4,464,176 | 8/1984 | Wijayarathna . |
| 4,531,943 | 7/1985 | Van Tassel et al. . |
| 4,551,292 | 11/1985 | Fletcher et al. . |
| 4,554,929 | 11/1985 | Samson et al. . |
| 4,563,181 | 1/1986 | Wijayarathna et al. . |
| 4,573,476 | 3/1986 | Ruiz et al. . |
| 4,577,543 | 3/1986 | Wilson . |
| 4,581,390 | 4/1986 | Flynn . |
| 4,592,341 | 6/1986 | Omagari et al. ............... 128/4 |
| 4,596,563 | 6/1986 | Pande . |
| 4,627,844 | 12/1986 | Schmitt . |
| 4,636,346 | 1/1987 | Gold et al. . |
| 4,639,252 | 1/1987 | Kelly et al. . |
| 4,661,094 | 4/1987 | Simpson . |
| 4,690,175 | 9/1987 | Ouchi et al. . |
| 4,739,768 | 4/1988 | Engelson . |
| 4,775,371 | 10/1988 | Mueller, Jr. . |
| 4,817,613 | 4/1989 | Jaraczewski et al. . |
| 4,840,622 | 6/1989 | Hardy . |
| 4,842,590 | 6/1989 | Tanabe et al. . |
| 4,863,442 | 9/1989 | De Mello et al. . |
| 4,886,506 | 12/1989 | Lovgren et al. . |
| 4,898,591 | 2/1990 | Jang et al. . |
| 4,899,787 | 2/1990 | Ouchi et al. . |
| 4,920,980 | 5/1990 | Jackowski . |
| 4,955,862 | 9/1990 | Sepetka . |
| 4,960,410 | 10/1990 | Pinchuk . |
| 4,976,690 | 12/1990 | Solar et al. . |
| 4,985,022 | 1/1991 | Fearnot et al. . |
| 5,017,259 | 5/1991 | Kohsai . |
| 5,034,005 | 7/1991 | Appling . |
| 5,045,072 | 9/1991 | Castillo et al. . |
| 5,047,045 | 9/1991 | Arney et al. . |
| 5,061,257 | 10/1991 | Martinez et al. . |
| 5,069,673 | 12/1991 | Shwab . |
| 5,069,674 | 12/1991 | Fearnot et al. . |
| 5,078,702 | 1/1992 | Pomeranz . |
| 5,085,649 | 2/1992 | Flynn . |
| 5,116,652 | 5/1992 | Alzner . |
| 5,156,592 | 10/1992 | Martin et al. . |
| 5,160,559 | 11/1992 | Scovil et al. . |
| 5,176,661 | 1/1993 | Evard et al. . |
| 5,184,627 | 2/1993 | de Toledo . |
| 5,221,270 | 6/1993 | Parker . |
| 5,254,107 | 10/1993 | Soltesz . |

FOREIGN PATENT DOCUMENTS

| | | |
|---|---|---|
| 0086498 | 8/1983 | European Pat. Off. . |
| 0117093 | 8/1984 | European Pat. Off. . |
| 0334640 | 9/1989 | European Pat. Off. . |
| 0369383 | 5/1990 | European Pat. Off. . |
| 0517075 | 12/1992 | European Pat. Off. . |
| 0531946 | 3/1993 | European Pat. Off. . |
| 2140755 | 4/1981 | Germany . |
| 51-49158 | 12/1976 | Japan . |
| 57-173065 | 10/1982 | Japan . |
| 60-31765 | 2/1985 | Japan . |
| 60-63065 | 4/1985 | Japan . |
| 60-500013 | 9/1985 | Japan . |
| 61-2870 | 1/1986 | Japan . |
| WO89/02763 | 4/1989 | WIPO . |
| WO92/11893 | 7/1992 | WIPO . |
| WO92/15356 | 9/1992 | WIPO . |
| WO92/17236 | 10/1992 | WIPO . |
| WO94/00170 | 1/1994 | WIPO . |

OTHER PUBLICATIONS

"Gall Bladder Necrosis After Transcatheter Hepatic C Arterial Embolization: A Technique to Avoid this Complication" by Hiroy Oshi Onodera, M.D., et al. *Radiology*, 152:209–210 (Jul. 1984).

Atlas of Human Anatomy, Frank H. Netter, M.D., 1989, plates 271 and 282.

(List continued on next page.)

*Primary Examiner*—Randy Shay

[57] ABSTRACT

A catheter for use with a guide wire which can be guided from an external body access site to an internal tissue, and into the tissue along a tortuous path of at least about 5 cm through vessels of less than about 3 mm lumen inner diameter. The catheter includes a relatively stiff proximal segment dimensioned to track the wire from the access site to a region adjacent the internal tissue, and a relatively flexible distal segment dimensioned to track the wire along the tortuous path within the soft tissue.

OTHER PUBLICATIONS

Berenstein, A., "Brachiocephalic vessel: Selective and superselective catheterization" *Radiology* (1983) 148:437–441.

McAuley, J. J., "Advances in guidewire technology" *Am. J. Cardiol.* (1984) 53:94C–96C.

Hinck, V. C., et al., "Simplified selective femorocerebral angiography" *Radiology* (1967) 89:1048–1052.

Doppman, J. L. et al., "The toposcopic catheter: A design for maneuvering through tortuous vessels" *Radiology* (1979) 132:735–737.

Guinto, Jr., F. C., "New catheter for tortuous vertebral artery" *AJNR* (1982) 3:85–86.

Goldstein, S. R. et al., "A miniature toposcopic catheter suitable for small diameter tortuous blood vessels" *J. Biomechan. Engin.* (1980) 102:221–229.

Rosen, R. J., "A new catheter for selective and superselective angiography" *Cardiovasc. Intervent. Radiol.* (1986) 9:49–51.

Target Therapeutics, Inc. v. SciMed Life Systems, Inc. and Cordis Endovascular Systems, Inc., Case No. C94-20775EAI (U.S.D.C., N.D. Cal) filed Nov. 10, 1994 Preliminary Injunction Documents.

Target Therapeutics, Inc. v. SciMed Life Systems, Inc. and Cordis Endovascular Systems, Inc., Case No. C94-20775EAI (U.S.D.C., N.D. Cal) filed Nov. 10, 1994 Motion to Stay Documents.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 12–14, 16–19, 21–28, 30–32 and 34–49 is confirmed.

Claims 1–11 were previously cancelled.

Claims 15, 20, 29 and 33 are determined to be patentable as amended.

15. The catheter of claim 14, where the lumen of the tubular member has a substantially uniform inner diameter along said distal [segments] *segment*.

20. The catheter of claim 12, [for use in accessing a site within the brain,] where the proximal segment [has a total length of between about 60–150 cm.,] *is of sufficient length, and at least 60 cm.*, and the distal segment [has a total length of between 10–15 cm] *is of sufficient length to access a target site within the brain.*

29. The catheter of claim [28 for use in accessing a site within the brain,] *26* where the proximal segment [has a total length of between about 60–150 cm,] *is of sufficient length, and at least 60 cm.*, and the distal segment [has a total length of between about 10–15 cm] *is of sufficient length to access a target site within the brain.*

33. The catheter of claim 31 where the proximal segment [has variable flexibility] *has increasing flexibility distally.*

* * * * *